US006610724B2

(12) United States Patent
Salvati et al.

(10) Patent No.: US 6,610,724 B2
(45) Date of Patent: Aug. 26, 2003

(54) 3-AMINOPYRAZOLE INHIBITORS OF CYCLIN DEPENDENT KINASES

(75) Inventors: Mark E. Salvati, Lawrenceville, NJ (US); S. David Kimball, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/219,844

(22) Filed: Aug. 15, 2002

(65) Prior Publication Data

US 2003/0018058 A1 Jan. 23, 2003

Related U.S. Application Data

(62) Division of application No. 09/777,273, filed on Feb. 6, 2001, now Pat. No. 6,482,842.
(60) Provisional application No. 60/180,609, filed on Feb. 7, 2000.

(51) Int. Cl.[7] .................... A61K 31/415; C07D 403/02; A61P 43/00
(52) U.S. Cl. ..................................... 514/397; 548/314.7
(58) Field of Search ........................ 548/314.7; 514/397

(56) References Cited

U.S. PATENT DOCUMENTS

| 4,416,683 A | 11/1983 | Burow, Jr. |
| 4,810,719 A | 3/1989 | Appleton et al. |
| 6,218,418 B1 | 4/2001 | Pevarello et al. |

FOREIGN PATENT DOCUMENTS

| EP | 0 919 244 A2 | 6/1999 |
| JP | 60-33552 | 2/1985 |
| JP | 62-10069 | 1/1987 |
| JP | 1-258695 | 10/1989 |
| WO | WO 93/05044 | 3/1993 |
| WO | WO 96/14843 | 5/1996 |
| WO | WO 98/11095 | 3/1998 |
| WO | WO 00/71532 A1 | 11/2000 |
| WO | WO 00/78299 A2 | 12/2000 |
| WO | WO 01/02369 A2 | 1/2001 |
| WO | WO 01/07411 A1 | 2/2001 |
| WO | WO 01/12188 A1 | 2/2001 |
| WO | WO 01/12189 A1 | 2/2001 |

OTHER PUBLICATIONS

*J. Biochem*, 117, 741–749 (1995).
*J. Cell Sci.*, 108, 2897 (1995).
Marshak et al., *J. of Cellular Biochemistry*, 45, 391–400 (1991).
Coleman et al., (1997) Identification of CDK4 Sequences Involved in Cyclin D, and p16 binding. *J. Biol. Chem.* 272, 30: 18869–18874.
Webster et al., Novel Drugs Targetin the Cell Cycle, Emerging Drugs (2000), 45–59.

MacLachlan et al.; Cyclins, Cyclin–Dependent Kinases and Cdk Inhibitors: Implications in Cell Cycle Control and Cander; Critical Reviews in Eukaryotic Gene Expression, 5(2): 127–156 (1995).

Paul Nurse; A Long Twentieth Century of the Cell Cycle and Beyond; Cell, vol. 100, 71–78, Jan. 7, 2000.

Joelle Fabron et al., "Synthese De Pyrazolo [1.5–a] Pyrimidines–F–Alkylees", Journal of Fluorine Chemistry, 51(1) (1991) pp. 141–148.

Raymond S. Brinkmeyer et al., "Dimerization of Pyrazolyl–5–hydroxypyrrolidinones to Tetrazocines", J. Heterocyclic Chem., 26(6), (1989), pp. 1713–1717.

J. Fabron et al., "Synthese Regiospecifique et Identification Spectrale de Nouveaux Amino Pyrazoles F–Alkyl Substitues", Journal of Flourine Chemistry, 37(3) (1987), pp. 371–386.

Z. Tanee Fomum, "Allenes. Part 39. The Synthesis of 3–Alkyl–5–aminopyrazoles and 3H–Indoles from Allenic or Acetylenic Nitriles," J. Chem. Soc., Perkin Trans. 1, (12), (1981), pp. 2997–3001.

Z.. T. Fomum et al., "Oxazolines, Thiazolines, Oxazoles, Thiazoles and Pyrazoles from Allenic and Acetylenic Nitriles", Tetrahedron Letters No. 13, (1975), pp. 1101–1104.

*Primary Examiner*—Joseph K. McKane
*Assistant Examiner*—Andrea D. Small
(74) *Attorney, Agent, or Firm*—Rena Patel

(57) ABSTRACT

The present invention describes compounds of formula I

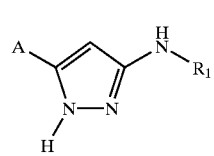

and pharmaceutically acceptable salts thereof.

The formula I compounds are protein kinase inhibitors and are useful in the treatment of proliferative diseases, for example, cancer, inflammation and arthritis. They may also be useful in the treatment of Alzheimer's disease, and cardiovascular disease.

25 Claims, No Drawings

3-AMINOPYRAZOLE INHIBITORS OF CYCLIN DEPENDENT KINASES

CROSS-REFERENCE TO RELATED APPLICATIONS

This application is a divisional application of U.S. application Ser. No. 09/777,273, filed on Feb. 6, 2001 now U.S. Pat. No. 6,482,842 B1 Nov. 19, 2002, which claims the benefit of Provisional application Ser. No. 60/180,609, filed Feb. 7, 2000.

BRIEF DESCRIPTION OF THE INVENTION

The present invention is directed to compounds of the formula

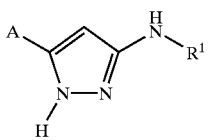

and pharmaceutically acceptable salts thereof. As used in formula I, and throughout the specification, the symbols have the following meanings:

$R^1=R^2$, $COR^3$, $CONH_2$, $CONR^2R^3$, $COOR^3$, or $SO_2R^3$;

$R^2$=H, alkyl, cycloalkyl, heterocycloalkyl, cycloalkylalkyl, heterocycloalkylalkyl, aryl, heteroaryl, arylalkyl, heteroarylalkyl, or heteroarylium;

$R^3$=alkyl, cycloalkyl, heterocycloalkyl, cycloalkylalkyl, heterocycloalkylalkyl, aryl, heteroaryl, arylalkyl, heteroarylalkyl;

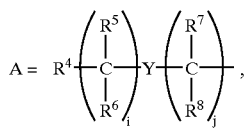

where i, j=0 or 1 but cannot both be 1, and Y=optionally substituted ethylene, alkene, alkyne, or any 2 adjacent carbon atoms of a cycloalkyl or cycloheteroalkyl ring of 3–7 atoms;

$R^4$=alkyl of 2 or more carbon atoms, cycloalkyl, heterocycloalkyl, cycloalkylalkyl, heterocycloalkylalkyl, alkyloxycarbonyl, aryl, heteroaryl, arylalkyl, heteroarylalkyl, aryloxycarbonyl, or $R^9$, provided that $R^4$ is other than an optionally substituted phenyl, pyridyl, pyrimidyl, pyrazinyl, pyridazinyl or piperidinyl ring;

$R^5$, $R^6$, $R^7$, $R^8$=independently H, alkyl, cycloalkyl, heterocycloalkyl, cycloalkylalkyl, heterocycloalkylalkyl, aryl, heteroaryl, arylalkyl, heteroarylalkyl, halo, or hydroxy, alkoxy, amino, $NR^{15}R^{16}$, thio, or alkylthio with the proviso that only one such heteroatom group is bonded to any one carbon atom;

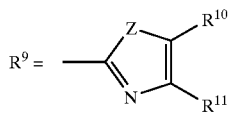

where Z=O, $NR^{12}$, or S;

$R^{10}$, $R^{11}$=independently H, alkyl, cycloalkyl, heterocycloalkyl, cycloalkylalkyl, heterocycloalkylalkyl, aryl, heteroaryl, arylalkyl, heteroarylalkyl, halo, hydroxy, alkoxy, alkylcarbonyloxy, carboxy, alkyloxycarbonyl, amino, $NR^{13}R^{14}$, carbamoyl, ureido, thio, or alkylthio; and $R^{12}$, $R^{13}$, $R^{14}$, $R^{15}$, and $R^{16}$=independently H, alkyl, cycloalkyl, heterocycloalkyl, cycloalkylalkyl, heterocycloalkylalkyl, aryl, heteroaryl, arylalkyl, or heteroarylalkyl.

The compounds of formula I are protein kinase inhibitors and are useful in the treatment of proliferative diseases, for example, cancer, inflammation and arthritis. They may also be useful in the treatment of Alzheimer's disease, and cardiovascular disease.

DESCRIPTION OF THE INVENTION

The present invention provides for compounds of formula I, pharmaceutical compositions employing such compounds, and for methods of using such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valences is assumed to have hydrogen atoms sufficient to satisfy the valences.

Carboxylate anion refers to a negatively charged group —COO⁻.

The term "alkyl" or "alk" refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—COOR), alkylcarbonyloxy (—OCOR), amino (—$NH_2$), carbamoyl (—NHCOOR— or —OCONHR—), urea (—NHCONHR—), amidinyl (—CNHNHR or —CNRNH₂), or thiol (—SH). Alkyl groups as defined may also comprise one or more carbon to carbon double bonds or one or more carbon to carbon triple bonds.

The term "alkenyl" refers to a hydrocarbon radical straight, branched or cyclic containing from 2 to 12 carbon atoms and at least one carbon to carbon double bond.

The term "alkynyl" refers to a hydrocarbon radical straight, branched or cyclic, containing from 2 to 12 carbon atoms and at least one carbon to carbon triple bond.

The term "ethylene" refers to a —CH$_2$CH$_2$— group.

Cycloalkyl is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

Sulfoxide and sulfone denote groups bonded by —SO— or —SO$_2$— linkages, respectively.

The term "alkyloxycarbonyl", as used herein, denotes an alkoxy group bonded through a carbonyl group. An alkoxycarbonyl radical is represented by the formula: —C(O)OR, where the R group is a straight or branched C$_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "arylalkyl", as used herein, denotes an aromatic ring bonded to an alkyl group as described above.

The term "aryl" refers to monocyclic or bicyclic aromatic rings, e.g. phenyl, substituted phenyl and the like, as well as groups which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, trifluoromethyl, amino, cycloalkyl, cyano, alkyl S(O)$_m$ (m=O, 1, 2), or thiol.

The term "heteroaryl" refers to a monocyclic aromatic hydrocarbon group having 5 or 6 ring atoms, a bicyclic aromatic group having 8 to 10 atoms, or a tricyclic aromatic group having 10 to 16 atoms, containing at least one heteroatom, O, S, or N, in which a carbon or nitrogen atom is the point of attachment, and in which one or two carbon atom(s) is optionally replaced by a heteroatom selected from O or S, or in which from 1 to 3 additional carbon atoms are optionally replaced by nitrogen heteroatoms, said heteroaryl group being optionally substituted as described herein. Exemplary heteroaryl groups include the following: thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, tetrazolyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents may include, but are not limited to, one or more of the following: halogen, alkyl, alkoxy, hydroxy, carboxy, carbamoyl, alkyloxycarbonyl, trifluoromethyl, cycloalkyl, nitro, cyano, amino, alkylS(O)$_m$ (m=0, 1, 2), or thiol.

The term "heteroarylium" refers to heteroaryl groups bearing a quaternary nitrogen atom and thus a positive charge.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms.

The term "quaternary nitrogen" refers to a tetravalent positively charged nitrogen atom including, e.g. the positively charged nitrogen in a tetraalkylammonium group (e.g. tetramethylammonium, N-methylpyridinium), the positively charged nitrogen in protonated ammonium species (e.g. trimethylhydroammonium, N-hydropyridinium), the positively charged nitrogen in amine N-oxides (e.g. N-methylmorpholine-N-oxide, pyridine-N-oxide), and the positively charged nitrogen in an N-amino-ammonium group (e.g. N-aminopyridinium).

The term "heteroatom" means O, S or N, selected on an independent basis.

The term "halogen" or "halo" refers to chlorine, bromine, fluorine or iodine.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

Suitable examples of salts of the compounds according to the invention with inorganic or organic acids are hydrochloride, hydrobromide, sulfate, phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

All configurational isomers of compounds of the present invention are contemplated, either in admixture or in pure or substantially pure form. The definition of compounds of the present invention very particularly embraces both cis (Z) and trans (E) alkene isomers, as well as cis and trans isomers of cycloalkyl or heterocycloalkyl rings.

Furthermore, with regard to the object compound I, it is to be understood that the compound includes tautomeric isomers. That is the compound of formula I may exist in either of the the following forms:

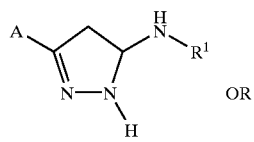

OR

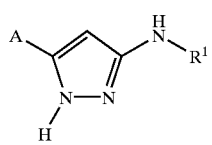

in a state of equilibrium.

It should be understood that solvates (e.g. hydrates) of the compounds of formula I are also within the scope of the present invention. Methods of solvation are generally known in the art. Accordingly, the compounds of the instant invention may be in the free or hydrate form, and may be obtained by methods exemplified by the following schemes.

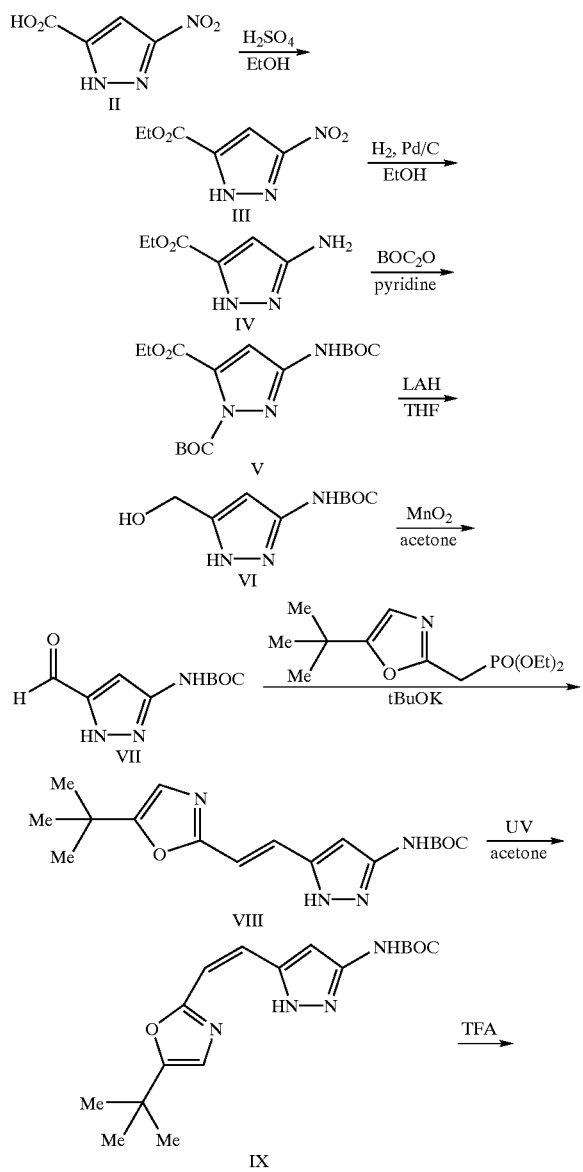

XI is a compound of formula I

As illustrated in Scheme I, a compound of formula III may be prepared by treating a solution of 5-nitro-3-pyrazole carboxylic acid (II) in absolute ethanol with $H_2SO_4$ to form the ester. The compound of formula IV may be prepared by treating nitro compound III with a reducing agent such as hydrogen in the presence of a catalyst such as palladium on charcoal, or with a metal reducing agent such as tin or iron. The amino group and one of the pyrazole ring nitrogen atoms are protected by treating a compound of formula IV with di-tert butyl dicarbonate or a comparable carbamylating agent and a base such as pyridine. The compond of formula V may be reduced with lithium aluminum hydride or a comparable reducing agent to give the alcohol VI, which may be oxidized by manganese dioxide or a comparable oxidizing agent to give an aldehyde of formula VII. The aldehyde of formula VII may be reacted with a phosphonate ester and a base such as potassium t-butoxide to provide an olefin of formula VIII. The olefin of formula VIII may be either cis (Z), trans (E) or a mixture of the two isomers. In the event that the compound of formula VIII is a single isomer, it may be equilibrated with its geometric olefin isomer by treatment with an agent such as ultraviolet light (UV) and acetone. In the specific instance illustrated the E alkene isomer VIII is interconverted with the Z alkene isomer IX. A compound of formula IX may be deprotected by treating with an acid such as trifluoroacetic acid or hydrochloric acid in a solvent such as dioxane to give the free amine X, which may be reacted with an acylating agent such as an isocyanate, acid anhydride, acid chloride, or the like, to give a compound of formula XI, which is a compound of formula I where $R^1$ is $CONR^2R^3$ and Y is Z alkenyl.

Scheme II

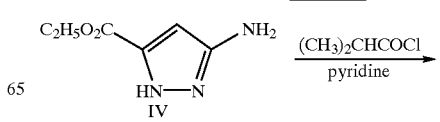

-continued

XII

XIII

XIV

XV

XVI

XV and XVI are compounds of formula I

According to Scheme II, a solution of 5-ethylcarboxylate-3-aminopyrazole IV, and a base such as pyridine may be reacted with an acid chloride such as 2-methyl butanoyl chloride to give the compound of formula XII. Treatment of a compound of formula XII with a reducing agent such as lithium aluminum hydride (LAH) in tetrahydrofuran (THF) gives the alcohol of formula XIII, which may be oxidized by an oxidant such as manganese dioxide in acetone to give an aldehyde of formula XIV. Aldehydes of formula XIV may be treated with a phosphonate ester in the presence of a base such as potassium tert-butoxide to give compounds of formula XV. Analogous to Scheme I, compounds of formula XV (which is a compound of formula I where Y is an E alkene) may be treated with ultraviolent light and acetone to give a compound of formula XVI (which is a compound of formula I where $R^1$ is $COR^3$ and Y is Z alkenyl).

Additional compounds of formula I where Y is an alkyne may be prepared by methods known to those of ordinary skill in the art. A compound of formula I where Y is an alkene may be reacted with a reducing agent such as hydrogen in the presence of a catalyst such as palladium on carbon to provide a compound of formula I where Y is ethylene. Compounds of formula I where Y is an alkyne may be prepared from the compound of formula I where Y is an alkene by methods known in the art, such as halogenation and dehydrohalogenation.

The starting compounds of Schemes I and II are commercially available or may be prepared by methods known to one of ordinary skill in the art.

The compounds shown in Schema I and II are illustrative, and the methods described may be used by those of ordinary skill in the art to prepare the analogous intermediates encompassed by the genus. All compounds of formula I may be prepared by modification of the procedures described herein.

A first group of preferred compounds of formula I are those where:

$R^1=R^2$, $COR^3$, or $CONR^2R^3$;

$R^2$=H, alkyl, aryl, heteroaryl, arylalkyl, or heteroarylalkyl;
$R^3$=alkyl, aryl, heteroaryl, arylalkyl, or heteroarylalkyl;

$$A = R^4 \left( \begin{array}{c} R^5 \\ | \\ C \\ | \\ R^6 \end{array} \right)_i Y \left( \begin{array}{c} R^7 \\ | \\ C \\ | \\ R^8 \end{array} \right)_j,$$

where i=j=0; Y=optionally substituted ethylene, alkene, or any two adjacent carbon atoms of a cycloalkyl ring;
$R^4$=alkyl of two or more carbon atoms, aryl, heteroaryl, or $R^9$;
$R^5$, $R^6$, $R^7$, $R^8$=independently H, or alkyl;

$R^9 =$ where Z=O; and
$R^{10}$, $R^{11}$=independently H, or alkyl.

A second group of preferred compounds of formula I are those where:

$R^1=CONR^2R^3$;

$R^2$=H, alkyl, heteroaryl, arylalkyl, or heteroarylalkyl;
$R^3$=aryl;

$$A = R^4 \left( \begin{array}{c} R^5 \\ | \\ C \\ | \\ R^6 \end{array} \right)_i Y \left( \begin{array}{c} R^7 \\ | \\ C \\ | \\ R^8 \end{array} \right)_j,$$

where i, j=0 or 1 but cannot both be 1, and Y=an optionally substituted ethylene or alkene;
$R^4=R^9$;
$R^5$, $R^6$, $R^7$, $R^8$=independently H, or alkyl;

$R^9 =$ where Z=O; and
$R^{10}$, $R^{11}$=independently H, or alkyl.

A third group of preferred compounds of formula I are those where:
$R^1=R^2$;
$R^2$=alkyl, cycloalkyl, heterocycloalkyl, aryl, heteroaryl, arylalkyl, or heteroarylalkyl;

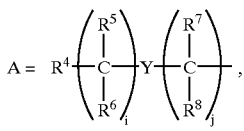

where i, j=0 or 1 but cannot both be 1, and Y=an optionally substituted ethylene or alkene;
$R^5$, $R^6$, $R^7$, $R^8$=independently H, or alkyl;
$R^4$=$R^9$;

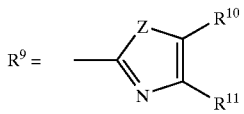

where Z=O;
$R^{10}$=alkyl; and
$R^{11}$=H.

A fourth group of preferred compounds of formula I are those where:

$R^1$=$COR^3$;

$R^3$=alkyl, cycloalkyl, heterocycloalkyl, cycloalkylalkyl, heterocycloalkylalkyl, aryl, heteroaryl, arylalkyl, or heteroarylalkyl;

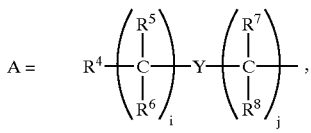

where i, j=0 or 1 but cannot both be 1, and Y=an optionally substituted ethylene, alkene or alkyne;
$R^4$=$R^9$;
$R^5$, $R^6$, $R^7$, $R^8$=independently H, or alkyl;

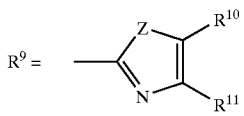

where Z=O;
$R^{10}$=alkyl; and
$R^{11}$=H.

Formula I compounds particularly useful in the methods of this invention include:

N,N-[(Z)-5-(2-(5-(1,1-dimethyl(ethyl))-oxazol-2-yl)vinyl)pyrazol-3-yl]2,6--difluorophenylaminocarbonyl amine;

N-[5-(2-(5-(1,1-dimethyl(ethyl))-oxazol-2-yl)vinyl)pyrazol-3-yl]2-(methyl)propanamide;

N-(Z)-[5-(2-(5-(1,1-dimethyl(ethyl))-oxazol-2-yl)vinyl)pyrazol-3-yl]2-(methyl)propanamide; and N,N-[(E)-5-(2-(5-(1,1-dimethyl(ethyl))-oxazol-2-yl)vinyl)pyrazol-3-yl]2,6-difluorophenylaminocarbonyl amine, among others.

The compounds according to the invention have pharmacological properties; in particular, the compounds of formula I are inhibitors of protein kinases such as the cyclin dependent kinases (cdks), for example, cdc2 (cdk1), cdk2, and cdk4. The novel compounds of formula I are expected to be useful in the therapy of proliferative diseases such as cancer, inflammation, arthritis, Alzheimer's disease and cardiovascular disease. These compounds may also be useful in the treatment of topical and systemic fungal infections.

More specifically, the compounds of formula I are useful in the treatment of a variety of cancers, including (but not limited to) the following:

carcinoma, including that of the bladder, breast, colon, kidney, liver, lung, ovary, pancreas, stomach, cervix, thyroid, prostate, and skin;

hematopoietic tumors of lymphoid lineage, including acute lymphocytic leukemia, B-cell lymphoma, and Burkett's lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal cellular proliferation, e.g., neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, angiogenesis, and endotoxic shock.

Compounds of formula I may also be useful in the treatment of Alzheimer's disease, as suggested by the recent finding that cdk5 is involved in the phosphorylation of tau protein (*J. Biochem*, 117, 741–749 (1995)).

Compounds of formula I may also act as inhibitors of other protein kinases, e.g., protein kinase C, her2, raf1, MEK1, MAP kinase, EGF receptor, PDGF receptor, IGF receptor, PI3 kinase, wee1 kinase, Src, Abl, VEGF, and 1ck, and thus be effective in the treatment of diseases associated with other protein kinases.

Compounds of formula I also induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with abberations in apoptosis including cancer (particularly, but not limited to follicular lymphomas, carcinomas with p53 mutations, hormone dependent tumors of the breast, prostate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus, erythematosus, immune mediated glomerulonephritis, rheumatoid arthritis, psoriasis, inflammatory bowel diseases, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention may also be useful in combination with known anti-cancer treatments such as radiation therapy or with cytostatic and cytotoxic agents, such as for example, but not limited to, DNA interactive agents, such as cisplatin or doxorubicin; inhibitors of farnesyl protein transferase, such as those described in pending U.S. application Ser. No. 08/802,329, topoisomerase II inhibitors, such as etoposide; topoisomerase I inhibitors, such as CPT-11 or topotecan; tubulin stabilizing agents, such as paclitaxel, docetaxel or the epothilones; hormonal agents, such as tamoxifen; thymidilate synthase inhibitors, such as 5-fluorouracil; and antimetabolites, such as methoxtrexate; antiangiogenic agents, such as angiostatin or endostatin; and kinase inhibitors, such as her2 specific antibodies. The formula I compounds of this invention may also be useful in combination with modulators of p53 transactivation. In addition, the formula I compounds may be used for treating chemotherapy-induced alopecia, chemotherapy-induced thrombocytopenia, chemotherapy-induced leukopenia or mucocitis. In the treatment of chemotherapy-induced alopecia, the formula I compound is preferably topically applied in the form of a medicament such as a gel, solution, dispersion or paste.

If formulated as a fixed dose, such combination products employ the compounds of this invention within the dosage range described below and the other pharmaceutically active agent within its approved dosage range. For example, the cdc2 inhibitor olomucine has been found to act synergistically with known cytotoxic agents in inducing apoptosis (*J. Cell Sci.*, 108, 2897 (1995)). Compounds of formula I may be used sequentially with known anti-cancer or cytotoxic agents when a combination formulation is inappropriate.

cdc2/cyclin B1 Kinase Assay cdc2/cyclin B1 kinase activity was determined by monitoring the incorporation of $^{32}$P into histone HI. The reaction consisted of 50 ng baculovirus expressed GST-cdc2, 75 ng baculovirus expressed GST-cyclin B1, 1 μg histone HI (Boehringer Mannheim), 0.2 μCi of $^{32}$P γ-ATP and 25 μM ATP in kinase buffer (50 mM Tris, pH 8.0, 10 mM MgCl$_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., *J. of Cellular Biochemistry*, 45, 391–400 (1991), incorporated by reference herein).

cdk2/cyclin E Kinase Assay cdk/cyclin E kinase activity was determined by monitoring the incorporation of $^{32}$P into the retinoblastoma protein. The reaction consisted of 2.5 ng baculovirus expressed GST-cdk2/cyclin E, 500 ng bacterially produced GST-retinoblastoma protein (aa 776–928), 0.2 μCi $^{32}$P γ-ATP and 25 μM ATP in kinase buffer (50 mM Hepes, pH 8.0, 10 mM MgCl$_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk 4/cyclin D1 Kinase Activity cdk4/cyclin D1 kinase activity was determined by monitoring the incorporation of $^{32}$P in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776–928), 0.2 μCi $^{32}$P γ-ATP and 25 μM ATP in kinase buffer (50 mM Hepes, pH 8.0, 10 mM MgCl$_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Wedster, K. R. (1997) Identification of CDK4 Sequences involved in cyclin D, and p16 binding. *J. Biol. Chem.* 272,30:18869–18874, incorporated by reference herein).

The following examples and preparations describe the manner and process of making and using the invention and are illustrative rather than limiting. It should be understood that there may be other embodiments which fall within the spirit and scope of the invention as defined by the claims appended hereto.

EXAMPLE 1

N,N-[(Z)-5-(2-(5-(1,1-dimethyl(ethyl))-oxazol-2-yl)vinyl) pyrazol-3-yl]2,6-difluorophenylaminocarbonyl amine (XI)

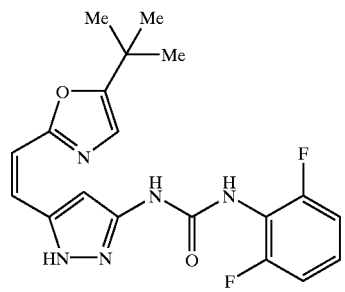

A. Preparation of 5-Nitro-3-pyrazole-ethylcarboxylate (III)

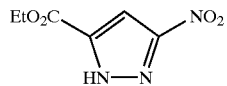

A solution of 10 g of 5-nitro-3-pyrazole carboxylic acid was heated to reflux in 50 ml of absolute ethanol and 2 ml of H$_2$SO$_4$. A Dean Stark trap was used to azeotrope the water produced. The solvent was removed under vacuum to give a white solid, which was used in the next step without further purification.

B. Preparation of 5-Carboxyethyl-3-aminopyrazole (IV)

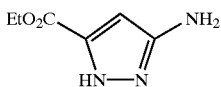

To a Parr bottle was added 300 mg of Pd/C (10%), 3 g of III and 125 ml of absolute ethanol. The hydrogenation was run at 30 psi for 4 hours, the catalyst removed by filtration through a cake of celite and the cake was washed with 30 ml of ethanol. To the ethanol solution was added 1 ml of HCl and then the solvent was taken to dryness under vacuum and the product was used in the next step without further purification.

C. Preparation of 5-Carboxyethyl-1,3-bis[1,1-dimethyl (ethyl)oxycarbonyl]-3-aminopyrazole (V)

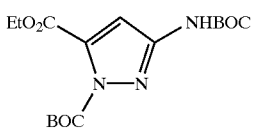

To a solution of IV in 50 ml of anhydrous pyridine was added 10.9 g of di-tertbutyldicarbonate. The reaction was heated to 95° C. for 12 hours and then the excess pyridine was removed under vacuum. The gum was taken up into 50 ml of pyridine and 11 g of di-tertbutyldicarbonate was added. The reaction was stirred for 1.5 hr at room temperature. The solvent was removed under vacuum and the orange/brown gum was dried under high vacuum overnight, and used in the next step without further purification.

D. Preparation of 5-Hydroxymethyl-3-[1,1-dimethyl(ethyl) oxycarbonyl]aminopyrazole (VI)

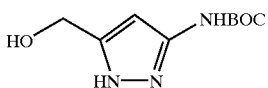

A solution consisting of 4.46 g of V in 100 ml of dry THF under a stream of N$_2$ was cooled to 0° C. with an ice bath. While keeping the temperature at 0° C., 37.69 ml of 1 M LiAlH$_4$ in THF was added to the THF solution over a period of 60 minutes. After stirring for 2 hours at 0° C., the solution was poured over 300 g of crushed ice. Once the ice had melted, the solution was brought to pH 7 by addition of HCl. The water layer was filtered to remove aluminum salts and the filtrate was extracted three times with 200 ml of ethyl acetate. The organic layer was collected, dried over MgSO$_4$ and evaporated to an orange solid. The solid was purified by silica gel chromatography to provide a total of 1.7 g of the alcohol (63%).

E. Preparation of 5-carboxaldehyde-3-[1,1-dimethyl(ethyl) oxycarbonyl]aminopyrazole (VII)

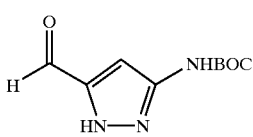

A solution consisting of 1.7 g of VI, 2.08 g of MnO$_2$ in 30 ml of acetone was heated at reflux for 24 hours. An additional 500 mg of MnO$_2$ was added and the reaction heated to reflux for an additional 3 hours. The mixture was filtered through a cake of Celite and the cake was washed with excess acetone. The solvent was removed to yield a brown solid, which was purified by crystallization from dichloromethane to provide 960 mg (57%) of the desired product in pure form.

F. Preparation of N,N-[5-(2-(5-(1,1-dimethyl(ethyl))-oxazol-2-yl)vinyl)pyrazol-3-yl]1,1-dimethyl(ethyl) oxycarbonyl amine (VIII)

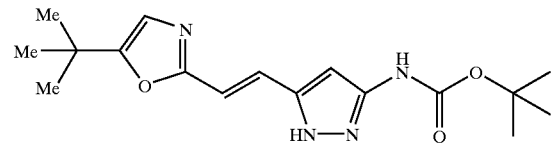

A solution of (5-t-butyl-oxazol-2-yl)methylphosphonic acid diethyl ester (0.88 g) in 10 ml of anhydrous THF under N$_2$ was cooled to 0° C. and 1.4 g of potassium tertbutoxide was added. The reaction was allowed to stir at 0° C. for 30 minutes at which time the anion solution was syringed into a solution of 960 mg of VII dissolved in 35 ml of anhydrous THF under N$_2$. The reaction was allowed to stir at room temperature for 1 hour at which point an additional portion of the anion solution (230 mg of the phosphonic acid ethyl ester mixed with 368 mg of potassium tertbutoxide as above) was added and the reaction was allowed to stir overnight at room temperature.

The solvent was removed under vacuum to give an orange solid and the desired product was purified by silica gel chromatography to give 1.2 g (93%) of the desired product as a tan solid. (M+H)$^+$=333. HPLC RT=4.17 min (YMC S5 ODS column, 4.6×50 mm; 10–90% MeOH/H$_2$O gradient,+ 0.1% TFA; 4 mL/min, 220 nM detection)

G. Preparation of N,N-[(Z)-5-(2-(5-(1,1-dimethyl(ethyl))-oxazol-2-yl)vinyl)pyrazol-3-yl]1,1-dimethyl(ethyl) oxycarbonyl amine (IX)

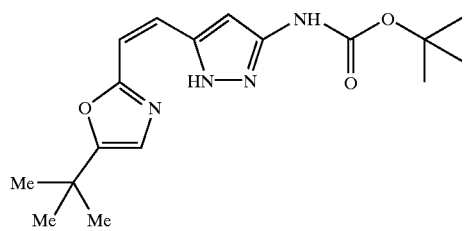

Into a jacketed 400 watt Hanovia mercury lamp was placed 312 mg of VIII in 20 ml of acetone and the reaction was irradiated for 24 hours to yield 82% of the desired Z isomer. The solvent was removed and the crude material was used in the next step.

H. Preparation of 3-amino-5-[(Z)-5-(1,1-dimethyl(ethyl)-oxazol-2-yl)vinyl]-2-yl pyrazole (X)

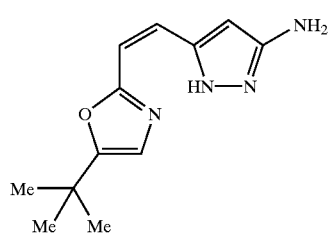

To a 0° C. solution of trifluoroacetic acid (2 ml) was added 1.26 g of IX, the reaction was allowed to warm to room temperature, and stirred at room temperature for 30 minutes.

The solvent was removed and the yellow residue was dried under high vacuum overnight to give the desired product in 84% yield. The desired product was used in the next step without further purification.

I. Preparation of N,N-[5-(2-(5-(1,1-dimethyl(ethyl))-oxazol-2-yl)vinyl)pyrazol-3-yl]2,6-difluorophenylaminocarbonyl amine (XI)

232 mg of the crude olefin X was taken up in 1 ml of dry pyridine and taken to dryness under vacuum. The oil was co-evaporated with dry acetonitrile to yield a pale yellow solid. The solid was taken up in 15 ml of chloroform and 1.3 ml of triethyl amine. To this solution was added 383 mg of 2,6-difluorophenyl isocyanate and the reaction heated to reflux overnight under a drying tube. The resulting product was purified by HPLC using a YMC S5 (ODS 20×100 mm) column to yield 89 mg of pure product. $(M+H)^+=388$. HPLC RT=4.22 min (YMC S5 ODS column, 4.6×50 mm; 10–90% MeOH/$H_2O$ gradient,+0.1% TFA; 4 mL/min, 220 nM detection).

EXAMPLE 2

N-[5-(2-(5-(1,1-dimethyl(ethyl))-oxazol-2-yl)vinyl)pyrazol-3-yl]2-(methyl)propanamide (XV)

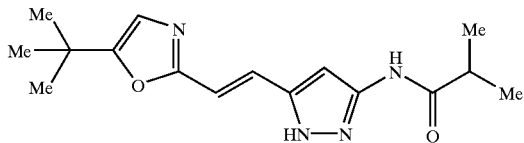

A. Preparation of 5-Carboxymethyl-3-(2-methyl(ethyl)carbonylamino)pyrazole (XII)

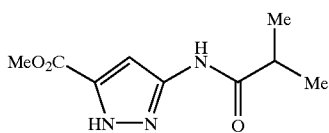

A solution consisting of 398 mg of 5-carboxymethyl-3-aminopyrazole (synthesized as described above for the 5-ethyl analog, by use of MeOH rather than EtOH in the esterification) and 440 mL of pyridine in 5 ml of anhydrous dioxane was cooled to 0° C. To this solution was slowly added 621 mL of 2-methylpropanoyl chloride. The reaction was allowed to stir at room temperature for two hours, diluted with 25 ml of chloroform and extracted once against 15 ml of 1 M HCl followed by 15 ml of saturated $NaHCO_3$. The organic layer was isolated and dried over $MgSO_4$ and the solvent was removed under vacuum. The product was used in the next step without further purification.

B. Preparation of 5-Hydroxymethyl-3-(2-methyl(ethyl)carbonylamino)pyrazole (XIII)

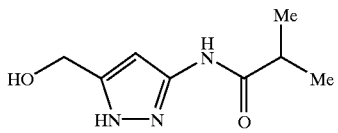

A solution of 787 mg of crude XII in 10 ml of dry THF was cooled to 0° C. in an ice bath. To this mixture was added 14 ml of 1 M $LiAlH_4$ in THF while maintaining the temperature at 0° C. The reaction was allowed to stir at 0° C. for 6.5 hours at which point the solution was poured over 100 g of crushed ice. Once the ice had melted, the solution was brought to pH 7 by addition of HCl. The water layer was filtered to remove aluminum salts and the filtrate was extracted three times with 75 ml of ethyl acetate. The organic layer was collected, dried over $MgSO_4$ and evaporated to an orange solid. The solid was purified on silica gel to give 79 mg of the alcohol (15%).

C. Preparation of 5-Carboxaldehyde-3-(2-methyl(ethyl)carbonylamino)pyrazole (XIV)

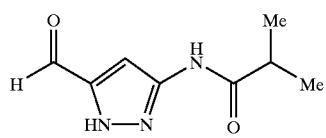

A solution consisting of 79 mg of XIII and 150 mg of $MnO_2$ in 10 ml of acetone was heated to reflux for 20 hours. The mixture was filtered through a cake of celite and the cake was washed with excess acetone. The solvent was removed to yield a brown solid, which was purified by silica gel to yield 58 mg (75%) of the desired product in pure form.

D. Preparation of N-(E)-[5-(2-(5-(1,1-dimethyl(ethyl))-oxazol-2-yl)vinyl)pyrazol-3-yl]-2-(methyl)propanamide (XV)

A solution of 110 mg of (5-t-butyl-oxazol-2-yl)methylphosphonic acid diethyl ester in 1 ml of anhydrous THF under $N_2$ was cooled to 0° C. and 800 ml of a 1 M THF solution of potassium tertbutoxide was added. The reaction was allowed to stir at 0° C. for 30 minutes at which time the anion solution was syringed into a solution of 29 mg of XIV dissolved in 1 ml of anhydrous THF under $N_2$. The reaction was allowed to stir at room temperature overnight. The solution was evaporated onto silica gel and the product was isolated by silica gel chromatography to give 16.6 mg (35%) of the desired product as a tan solid. $(M+H)^+=303$. HPLC RT=3.51 min (YMC S5 ODS column, 4.6×50 mm; 10–90% MeOH/$H_2O$ gradient,+0.1% TFA; 4 mL/min, 220 nM detection).

EXAMPLE 3

N-(Z)-[5-(2-(5-(1,1-dimethyl(ethyl))-oxazol-2-yl)vinyl)pyrazol-3-yl]2-(methyl)propanamide (XVI)

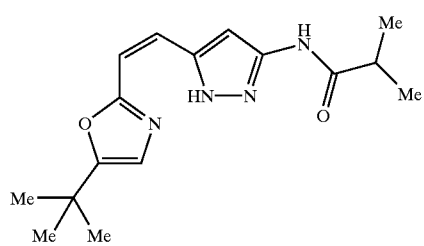

A solution of 32 mg of XV (described in Example 2) dissolved in 700 μl of acetone in a glass tube was irradiated for 3 days with an UV lamp to yield a 97% conversion to the E olefin isomer. The product was purified by silica gel chromatography to give 21 mg of the desired product. $(M+H)^+=303$. HPLC RT=3.72 min (YMC S5 ODS column, 4.6×50 mm; 10–90% MeOH/$H_2O$ gradient,+0.1% TFA; 4 mL/min, 220 nM detection).

EXAMPLE 4

N,N-[(E)-5-(2-(5-(1,1-dimethyl(ethyl))-oxazol-2-yl)vinyl)pyrazol-3-yl]2,6-difluorophenylaminocarbonyl amine (XVII)

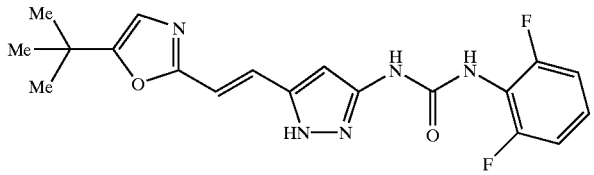

The above compound was prepared following procedures analogous to those described in Example 1. (M+H)⁺=388. HPLC RT=3.62 min (YMC S5 ODS column, 4.6×50 mm; 10–90% MeOH/H$_2$O gradient,+0.1% TFA; 4 mL/min, 220 nM detection).

We claim:

1. A compound of the formula:

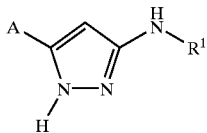

I and pharmaceutically acceptable salts thereof wherein:

R$^1$ is R$^2$, COR$^3$, CONH$_2$, CONR$^2$R$^3$, COOR$^3$, or SO$_2$R$^3$;

R$^2$ is H, alkyl, cycloalkyl, heterocycloalkyl, cycloalkylalkyl, heterocycloalkylalkyl, aryl, heteroaryl, arylalkyl, heteroarylalkyl, or heteroarylium;

R$^3$ is alkyl, cycloalkyl, heterocycloalkyl, cycloalkylalkyl, heterocycloalkylalkyl, aryl, heteroaryl, arylalkyl, heteroarylalkyl;

A is

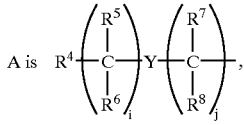

wherein i, j=0 or 1 but cannot both be 1, and Y is optionally substituted ethylene, alkene, alkyne, or any 2 adjacent carbon atoms of a cycloalkyl or cycloheteroalkyl ring of 3–7 atoms;

R$^4$ is R$^9$;

each R$^5$, R$^6$, R$^7$, R$^8$ is, independently, H, alkyl, cycloalkyl, heterocycloalkyl, cycloalkylalkyl, heterocycloalkylalkyl, aryl, heteroaryl, arylalkyl, heteroarylalkyl, halo, or hydroxy, alkoxy, amino, NR$^{15}$R$^{16}$, thio, or alkylthio with the proviso that only one such heteroatom group is bonded to any one carbon atom;

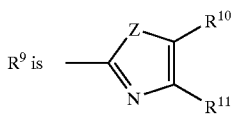

wherein Z is NR$^{12}$;

each R$^{10}$, R$^{11}$ is, independently, H, alkyl, cycloalkyl, heterocycloalkyl, cycloalkylalkyl, heterocycloalkylalkyl, aryl, heteroaryl, arylalkyl, heteroarylalkyl, halo, hydroxy, alkoxy, alkylcarbonyloxy, carboxy, alkyloxycarbonyl, amino, NR$^{13}$R$^{14}$, carbamoyl, ureido, thio, or alkylthio; and each R$^{12}$, R$^{13}$, R$^{14}$, R$^{15}$, and R$^{16}$ is, independently, H, alkyl, cycloalkyl, heterocycloalkyl, cycloalkylalkyl, heterocycloalkylalkyl, aryl, heteroaryl, arylalkyl, or heteroarylalkyl.

2. A pharmaceutical composition comprising a compound of claim 1 and a pharmaceutically acceptable carrier.

3. A pharmaceutical composition comprising a compound of claim 1 in combination with a pharmaceutically acceptable carrier and an anti-cancer agent formulated as a fixed dose.

4. A pharmaceutical composition comprising a compound of claim 1 in combination with a pharmaceutically acceptable carrier and a modulator of p53 transactivation formulated at a fixed dose.

5. A method of modulating apoptosis which comprises administering to a mammalian specie in need thereof an effective apoptosis modulating amount of a compound of claim 1.

6. A method of inhibiting protein kinases which comprises administering to a mammalian specie in need thereof an effective protein kinase inhibiting amount of a compound of claim 1.

7. A method of inhibiting cyclin dependent kinases which comprises administering to a mammalian specie in need thereof an effective cyclin dependent kinase inhibiting amount of a compound of claim 1.

8. A method of inhibiting cdc2 (cdk1) which comprises administering to a mammalian specie in need thereof an effective cdc2 inhibiting amount of a compound of claim 1.

9. A method of inhibiting cdk2 which comprises administering to a mammalian specie in need thereof an effective cdk2 inhibiting amount of a compound of claim 1.

10. A method of inhibiting cdk3 which comprises administering to a mammalian specie in need thereof an effective cdk3 inhibiting amount of a compound of claim 1.

11. A method of inhibiting cdk4 which comprises administering to a mammalian specie in need thereof an effective cdk4 inhibiting amount of a compound of claim 1.

12. A method of inhibiting cdk5 which comprises administering to a mammalian specie in need thereof an effective cdk5 inhibiting amount of a compound of claim 1.

13. A method of inhibiting cdk6 which comprises administering to a mammalian specie in need thereof an effective cdk6 inhibiting amount of a compound of claim 1.

14. A method of inhibiting cdk7 which comprises administering to a mammalian specie in need thereof an effective cdk7 inhibiting amount of a compound of claim 1.

15. A method of inhibiting cdk8 which comprises administering to a mammalian specie in need thereof an effective cdk8 inhibiting amount of a compound of claim 1.

16. A method for treating proliferative diseases comprising administering to a mammalian specie in need thereof a therapeutically effective amount of a composition of claim 2.

17. A method for treating cancer comprising administering to a mammalian specie in need thereof a therapeutically effective amount of a composition of claim 2.

18. A method for treating inflammation, inflamatory bowel disease, or transplantation rejection, comprising administering to a mammalian specie in need thereof a therapeutically effective amount of a composition of claim 2.

19. A method for treating arthritis comprising administering to a mammalian specie in need thereof a therapeutically effective amount of a composition of claim 2.

20. A method for treating proliferative diseases comprising administering to a mammalian specie in need thereof a therapeutically effective amount of a composition of claim 3.

21. A method for treating cancer comprising administering to a mammalian specie in need thereof a therapeutically effective amount of a composition of claim 8.

22. A method for treating proliferative diseases comprising administering to a mammalian specie in need thereof a therapeutically effective amount of a composition of claim 4.

23. A method for treating cancer comprising administering to a mammalian specie in need thereof a therapeutically effective amount of a composition of claim 4.

24. A method for the treatment of a cyclin dependent kinase-associated disorder, comprising administering to a subject in need thereof an amount effective therefor of at least one compound of claim 1.

25. A method for treating chemotherapy-induced alopecia, chemotherapy-induced thrombocytopenia, chemotherapy-induced leukopenia or mucocitis which comprises administering to a mammalian specie in need thereof a therapeutically effective amount of a compound of claim 1.

* * * * *